United States Patent [19]

Tzikas

[11] 4,202,827
[45] May 13, 1980

[54] PROCESS FOR THE PRODUCTION OF 1-ANTHRAQUINONYL HYDRAZINE

[75] Inventor: Athanassios Tzikas, Pratteln, Switzerland

[73] Assignee: Ciba-Geigy Corporation, Ardsley, N.Y.

[21] Appl. No.: 935,035

[22] Filed: Aug. 18, 1978

[30] Foreign Application Priority Data

Sep. 2, 1977 [CH] Switzerland ..................... 10735/77

[51] Int. Cl.$^2$ ................... C07C 109/04; C07C 103/75
[52] U.S. Cl. .............................. 260/378; 260/558 H
[58] Field of Search ............ 260/378, 360, 509, 558 H

[56] References Cited

FOREIGN PATENT DOCUMENTS

| | | |
|---|---|---|
| 163447 | 8/1904 | Fed. Rep. of Germany . |
| 171293 | 8/1904 | Fed. Rep. of Germany . |
| 2452413 | 5/1976 | Fed. Rep. of Germany . |
| 50-330 | 6/1975 | Japan ........................................ 260/569 |

OTHER PUBLICATIONS

Principles of Organic Synthesis, pp. 407–413, R.O.C. Norman.
"The Chemistry of Synthetic Dyes", vol. II, 1952, K. Vankaterman, pp. 993–996, Academic Press Inc., N.Y.
"Grundlagen der Synthese von Zwichen Produkten und Farbstoffen", p. 918, 1966, Nikolai Niworoshzow, Akademie-Verlag, Berlin.
Chemical Abstract, vol. 61, #4515f, "Reactive Dyes Containing Hydrazine Groups", by Yamase et al., 1964.
Anthracene and Anthraquinone, pp. 192 & 196, & 363–364, by E. de Barry Barnett, 1921, D. Van Nostrand Company, New York, N.Y.

Primary Examiner—Winston A. Douglas
Assistant Examiner—Raymond K. Covington
Attorney, Agent, or Firm—Prabodh I. Almaula

[57] ABSTRACT

A process for the production of 1-anthraquinonyl hydrazines of the formula

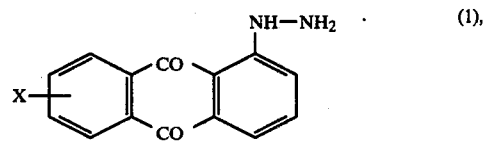

(1), wherein X is hydrogen or —NH—NH$_2$, which comprises reacting 1-nitroanthraquinones of the formula

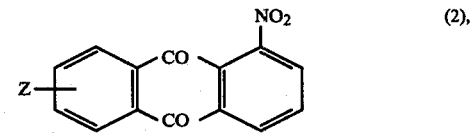

(2), wherein Z is hydrogen or nitro, in aprotic dipolar solvents, with hydrazine or hydrazine hydrate, at normal or slightly elevated temperature, to give 1-anthraquinonyl hydrazines of the formula (1).

3 Claims, No Drawings

PROCESS FOR THE PRODUCTION OF 1-ANTHRAQUINONYL HYDRAZINE

The present invention relates to a process for the production of 1-anthraquinonyl hydrazines of the formula

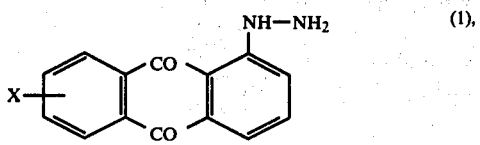

wherein X is hydrogen or —NH—NH$_2$, which comprises reacting 1-nitroanthraquinones of the formula

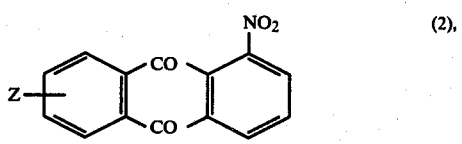

wherein Z is hydrogen or nitro, in aprotic dipolar solvents, with hydrazine or hydrazine hydrate at normal or slightly elevated temperature, to give 1-anthraquinonyl hydrazines of the formula (1).

Examples of 1-nitroanthraquinones of the formula (2) which can be used as starting compounds for the process of the present invention are: 1-nitroanthraquinone, 1,5-dinitroanthraquinone, 1,6-dinitroanthraquinone, 1,8-dinitroanthraquinone.

Examples of aprotic dipolar solvents are: N-methyl-2-pyrrolidone, tetramethylurea, sulfolane, hexamethylphosphoric triamide, dimethyl sulfoxide, dimethyl acetamide, diethyl acetamide, acetonitrile, dimethyl formamide, 3,3'-thiodipropionitrile and also pyridine.

Nitrite which forms during the reaction can be destroyed by adding urea or reagents having a similar action to the reaction mixture.

The process of the present invention is normally carried out at room temperature. During the reaction, the temperature of the reaction mixture rises to 30°–40° C. The reaction can also be initiated above room temperature (e.g. at 30° C.) or below room temperature (e.g. at 5° to 10° C.). The advantageous temperature range for the reaction is that from about 0° to 50° C.

A preferred embodiment of the process of the invention consists in reacting 1-nitroanthraquinone in N-methyl-2-pyrrolidone, tetramethyl urea or sulfolane, with hydrazine hydrate at room temperature to give 1-anthraquinonyl hydrazine of the formula

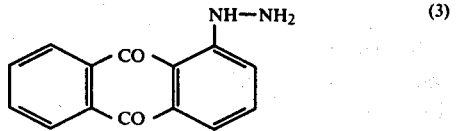

The 1-anthraquinonyl hydrazines of the formula (1) are important intermediates for the production of pyrazolanthrone and a number of its derivatives. Pyrazolanthrone in its turn is used as starting material for the synthesis of valuable vat dyes. Pyrazolanthrone is obtained by cyclisation of 1-anthraquinonyl hydrazine, which according to the prior art can be obtained either from 1-chloroanthraquinone and hydrazine or from, diazotised 1-aminoanthraquinone by reduction. However, both these processes for the production of 1-anthraquinonyl hydrazine are complicated and expensive, as the starting compounds 1-chloroanthraquinone and 1-aminoanthraquinone must first be obtained via anthraquinone-1-sulphonic acid. Now that methods for the large-scale production of 1-nitroanthraquinone by the direct nitration of anthraquinone are meanwhile available, and that consequently 1-nitroanthraquinone has become a readily obtainable starting compound, the process of the present invention affords a more direct and thus technically more advantageous method of producing 1-anthraquinonyl hydrazines. The cyclisation of 1-anthraquinonyl hydrazine to pyrazolanthrone is effected by heating in strong mineral acids, for example sulphuric acid.

The invention is illustrated by the following Examples, in which the parts are by weight.

EXAMPLE 1

25.3 parts of 1-nitroanthraquinone are suspended at room temperature in 100 parts of N-methyl-2-pyrrolidone. Then 8 parts of hydrazine hydrate, dissolved in 40 parts of N-methyl-2-pyrrolidone, are added dropwise to this suspension in the course of 1 hour, whereupon the temperature rises to 38° C. The reaction mixture is stirred for ½ hour and filtered after the addition of 300 parts of a mixture of ice and water. The filter cake is washed neutral with water.

Yield: 24.5 parts of 1-anthraquinonyl hydrazine of the formula (3).

EXAMPLE 2

25.3 parts of 1-nitroanthraquinone are suspended at room temperature in 100 parts of tetramethylurea. Then 8 parts of hydrazine hydrate, dissolved in 40 parts of tetramethylurea, are added dropwise to this suspension in the course of 1 hour, whereupon the temperature rises to 36° C. Then the reaction mixture is stirred for ½ hour and filtered after the addition of 300 parts of a mixture of ice and water. The filter cake is washed neutral with water.

Yield: 24 parts of 1-anthraquinonyl hydrazine of the formula (3).

EXAMPLE 3

25.3 parts of 1-nitroanthraquinone are suspended at room temperature in 100 parts of sulfolane. Then 8 parts of hydrazine hydrate, dissolved in 40 parts of sulfolane, are added dropwise to this suspension in the course of 1 hour, whereupon the temperature rises to 35° C. The reaction mixture is then stirred for ½ hour and filtered after the addition of 300 parts of a mixture of ice and water. The filter cake is washed neutral with water.

Yield: 24 parts of 1-anthraquinonyl hydrazine of the formula (3).

EXAMPLE 4

10 parts of 1-nitroanthraquinone and 5 parts of urea are suspended at room temperature in 50 parts of sulfolane. Then 4 parts of hydrazine hydrate, dissolved in 20 parts of sulfolane, are added dropwise to this suspension in the course of 1 hour, whereupon the temperature rises to 35° C. The reaction mixture is stirred for ½ hour and filtered after the addition of 200 parts of a mixture of ice and water. The filter cake is washed neutral with water.

Yield: 8.4 parts of 1-anthraquinonyl hydrazine of the formula (3).

EXAMPLE 5

10 parts of 1-nitroanthraquinone are suspended at room temperature in 50 parts of sulfolane. Then 4 parts of hydrazine hydrate, dissolved in 20 parts of sulfolane, are added dropwise to this suspension in the course of 1 hour, whereupon the temperature rises to 40°–45° C. After addition of 200 parts of a mixture of ice and water, the reaction mixture is filtered and the filter cake washed neutral with water.

Yield: 8 parts of 1-anthraquinonyl hydrazine of the formula (3).

EXAMPLE 6

10 parts of 1-nitroanthraquinone and 5 parts of urea are suspended at room temperature in 50 parts of N-methyl-2-pyrrolidone. Then 4 parts of hydrazine hydrate, dissolved in 20 parts of N-methyl-2-pyrrolidone, are added dropwise to this suspension in the course of 1 hour, whereupon the temperature rises to 38° C. The reaction mixture is stirred for ½ hour and filtered after the addition of 200 parts of a mixture of ice and water. The filter cake is washed neutral with water.

Yield: 7.8 parts of 1-anthraquinonyl hydrazine of the formula (3).

EXAMPLE 7

10 parts of 1-nitroanthraquinone are suspended at room temperature in 50 parts of N-methyl-2-pyrrolidone. Then 4 parts of hydrazine hydrate, dissolved in 20 parts of N-methyl-2-pyrrolidone, are added dropwise to this suspension at 45° C. in the course of 2 hours, whereupon the temperature rises to 50° C. After addition of 200 parts of a mixture of ice and water, the reaction mixture is filtered and the filter cake washed neutral with water.

Yield: 8 parts of 1-anthraquinonyl hydrazine of the formula (3).

EXAMPLE 8

10 parts of 1-nitroanthraquinone are suspended at room temperature in 50 parts of dimethyl sulfoxide. Then 4 parts of hydrazine hydrate, dissolved in 20 parts of dimethyl sulfoxide, are added dropwise to this suspension in the course of 1 hour, whereupon the temperature rises to 28° C. The reaction mixture is stirred for ½ hour and filtered after the addition of 200 parts of a mixture of ice and water. The filter cake is washed neutral with water.

Yield: 7 parts of 1-anthraquinonyl hydrazine of the formula (3).

EXAMPLE 9

10 parts of 1-nitroanthraquinone are dissolved at 50° C. in 60 parts of 3,3'-thiodipropionitrile. Then 4 parts of hydrazine hydrate are added dropwise at the same temperature (50° C.) to this suspension in the course of 1 hour, whereupon the temperature rises to 60° C. After addition of 200 parts of a mixture of ice and water, the reaction mixture is filtered and the filter cake is washed neutral with water.

Yield: 8.2 parts of 1-anthraquinonyl hydrazine of the formula (3).

EXAMPLE 10

10 parts of 1-nitroanthraquinone are suspended at room temperature in 60 parts of hexamethylphosphoric triamide. Then 4 parts of hydrazine hydrate, dissolved in 20 parts of hexamethylphosphoric triamide, are added dropwise to this suspension in the course of 2 hours, whereupon the temperature rises to 40° C. The reaction mixture is then stirred for 10 minutes and filtered after the addition of 200 parts of a mixture of ice and water. The filter cake is washed neutral with water.

Yield: 7 parts of 1-anthraquinonyl hydrazine of the formula (3).

EXAMPLE 11

10 parts of 1-nitroanthraquinone are suspended at room temperature in 60 parts of hexamethylphosphoric triamide. Then 4 parts of hydrazine hydrate, dissolved in 20 parts of hexamethylphosphoric triamide, are added dropwise to this suspension in the course of 2 hours, while keeping the temperature at 25° C. The reaction mixture is then stirred and filtered after the addition of 200 parts of a mixture of ice and water. The filter cake is washed neutral with water.

Yield: 7 parts of 1-anthraquinonyl hydrazine of the formula (3).

EXAMPLE 12

To 55 parts of a moist filter cake containing 24 parts of 1-anthraquinonyl hydrazine (dry weight) obtained by the the procedure described in any one of Examples 1 to 11 are added 150 parts by volume of concentrated sulfuric acid, such that the temperature does not rise above 100° C. (about ½ hour). The reaction mixture is then stirred for 2 hours at 100° to 110° C., subsequently cooled to 40° C. and diluted dropwise with 150 parts by volume of water. The suspension is then poured into a mixture of ice and water and filtered. The filter cake is washed neutral with water and dried, affording 22.2 parts of pyrazolanthrone of the formula.

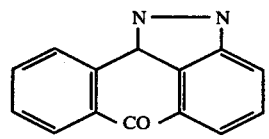

(4).

EXAMPLE 13

10 parts of 1,5-dinitroanthraquinone are suspended at room temperature in 50 parts of N-methyl-2-pyrrolidone. The suspension is heated to 45°–50° C. and then 7 parts of hydrazine hydrate, dissolved in 30 parts of N-methyl-2-pyrrolidone, are added dropwise in the course of 2 hours at this temperature. The reaction mixture is stirred for 10 minutes and filtered after the addition of 200 parts of a mixture of ice and water. The filter cake is washed neutral with water.

Yield: 7 parts of 1,5-dianthraquinonyl hydrazine of the formula

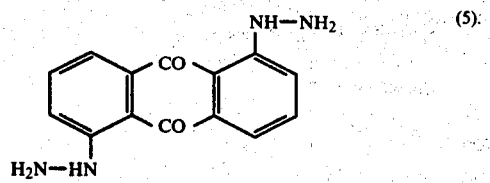

(5)

EXAMPLE 14

10 parts of 1,5-dinitroanthraquinone are suspended at room temperature in 60 parts of N-methyl-2-pyrrolidone. Then 7 parts of hydrazine hydrate, dissolved in 30 parts of N-methyl-2-pyrrolidone, are added dropwise to this suspension in the course of 2 hours, whereupon the temperature rises to 36° C. The reaction mixture is stirred for ½ hour and filtered after the addition of 200 parts of a mixture of ice and water. The filter cake is washed neutral with water.

Yield: 7 parts of 1,5-dianthraquinonyl hydrazine of the formula (5).

EXAMPLE 15

10 parts of 1,5-dinitroanthraquinone and 10 parts of urea are suspended at room temperature in 60 parts of N-methyl-2-pyrrolidone. Then 7 parts of hydrazine hydrate, dissolved in 30 parts of N-methyl-2-pyrrolidone, are added dropwise to this suspension in the course of 2 hours, whereupon the temperature rises to 36° C. The reaction mixture is stirred for ½ hour and filtered after the addition of 200 parts of a mixture of ice and water. The filter cake is washed neutral with water.

Yield: 7 parts of 1,5-dianthraquinonyl hydrazine of the formula (5).

EXAMPLE 16

10 parts of 1,5-dinitroanthraquinone are suspended at room temperature in 60 parts of sulfolane. The suspension is heated to 50° C. and then 7 parts of hydrazine hydrate, dissolved in 30 parts of sulfolane, are added dropwise at this temperature in the course of 2 hours. The reaction mixture is stirred for 10 minutes and filtered after the addition of 200 parts of a mixture of ice and water. The filter cake is washed neutral with water.

Yield: 7.2 parts of 1,5-dianthraquinonyl hydrazine of the formula (5).

EXAMPLE 17

10 parts of 1,5-dinitroanthraquinone are suspended at room temperature in 60 parts of sulfolane. Then 7 parts of hydrazine hydrate, dissolved in 30 parts of sulfolane, are added dropwise to this suspension in the course of 2 hours, whereupon the temperature rises to 30° C. The reaction mixture is stirred for ½ hour and filtered after the addition of 200 parts of a mixture of ice and water. The filter cake is washed neutral with water.

Yield: 7.2 parts of 1,5-dianthraquinonyl hydrazine of the formula (5).

EXAMPLE 18

10 parts of 1,8-dinitroanthraquinone are suspended at room temperature in 50 parts of N-methyl-2-pyrrolidone. The suspension is heated to 45°–50° C., then 7 parts of hydrazine hydrate, dissolved in 30 parts of N-methyl-2-pyrrolidone, are added dropwise at this temperature in the course of 2 hours. The reaction mixture is stirred for 10 minutes and filtered after the addition of 200 parts of a mixture of ice and water. The filter cake is washed neutral with water.

Yield: 6.8 parts of 1,8-dianthraquinonyl hydrazine of the formula

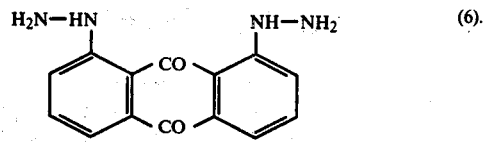

(6)

EXAMPLE 19

10 parts of 1,8-dinitroanthraquinone are suspended at room temperature in 60 parts of N-methyl-2-pyrrolidone. Then 7 parts of hydrazine hydrate, dissolved in 30 parts of N-methyl-2-pyrrolidone, are added dropwise to this suspension in the course of 2 hours, whereupon the temperature rises to 36° C. The reaction mixture is then stirred for ½ hour and filtered after the addition of 200 parts of a mixture of ice and water. The filter cake is washed neutral with water.

Yield: 6.5 parts of 1,8-dianthraquinonyl hydrazine of the formula (6).

EXAMPLE 20

10 parts of 1,8-dinitroanthraquinone and 10 parts of urea are suspended at room temperature in 60 parts of N-methyl-2-pyrrolidone. Then 7 parts of hydrazine hydrate, dissolved in 30 parts of N-methyl-2-pyrrolidone, are added dropwise to this suspension in the course of 2 hours, whereupon the temperature rises to 36° C. The reaction mixture is stirred for ½ hour and filtered after the addition of 200 parts of a mixture of ice and water. The filter cake is washed neutral with water.

Yield: 7 parts of 1,8-dianthraquinonyl hydrazine of the formula (6).

EXAMPLE 21

10 parts of 1,8-dinitroanthraquinone are suspended at room temperature in 60 parts of sulfolane. The suspension is heated to 50° C., then 7 parts of hydrazine hydrate, dissolved in 30 parts of sulfolane, are added dropwise in the course of 2 hours. The reaction mixture is stirred for ½ hour and filtered after the addition of 200 parts of a mixture of ice and water. The filter cake is washed neutral with water.

Yield: 7 parts of 1,8-dianthraquinonyl hydrazine of the formula (6).

EXAMPLE 22

10 parts of 1,8-dinitroanthraquinone are suspended at room temperature in 60 parts of sulfolane. Then 7 parts of hydrazine hydrate, dissolved in 30 parts of sulfolane, are added dropwise to this suspension in the course of 2 hours, whereupon the temperature rises to 30° C. The reaction mixture is then stirred for ½ hour and filtered after the addition of 200 parts of a mixture of ice and water. The filter cake is washed neutral with water.

Yield: 7 parts of 1,8-dianthraquinonyl hydrazine of the formula (6).

What is claimed is:
1. A process for the production of 1-anthraquinonyl hydrazines of the formula

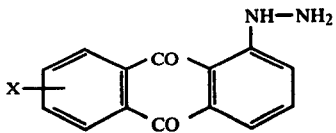

wherein X is hydrogen or —NH—NH$_2$, which comprises reacting 1-nitroanthraquinones of the formula

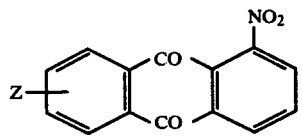

wherein Z is hydrogen or nitro, in aprotic dipolar solvents, with hydrazine or hydrazine hydrate, at normal or slightly elevated temperature, to give 1-anthraquinonyl hydrazines of the formula (1).

2. A process according to claim 1, wherein 1-nitroanthraquinone is reacted in N-methyl-2-pyrrolidone, tetramethylurea or sulfolane, with hydrazine hydrate at room temperature to give 1-anthraquinonyl hydrazine of the formula

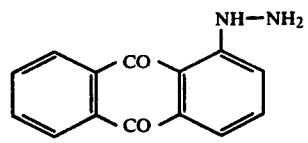

3. The 1-anthraquinonyl hydrazines obtained by the process according to claim 1.

* * * * *